US 7,879,314 B2

(12) United States Patent
Licha et al.

(10) Patent No.: US 7,879,314 B2
(45) Date of Patent: Feb. 1, 2011

(54) OPTICAL IMAGING OF RHEUMATOID ARTHRITIS

(75) Inventors: Kai Licha, Falkensee (DE); Michael Schirner, Berlin (DE); Axel Vater, Berlin (DE); Sonja Vollmer, Kleinmachnow (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 11/476,218

(22) Filed: Jun. 28, 2006

(65) Prior Publication Data

US 2007/0059244 A1    Mar. 15, 2007

Related U.S. Application Data

(60) Provisional application No. 60/694,669, filed on Jun. 29, 2005.

(30) Foreign Application Priority Data

Jul. 14, 2005  (EP)  ................................... 05015365

(51) Int. Cl.
*A61B 5/00* (2006.01)
*A61B 8/00* (2006.01)
*A61B 10/00* (2006.01)
*A61K 49/00* (2006.01)

(52) U.S. Cl. ........................................ 424/9.1; 424/9.6

(58) Field of Classification Search ................ 424/9.6
See application file for complete search history.

(56) References Cited

U.S. PATENT DOCUMENTS 6,534,041 B1 * 3/2003 Licha et al. .................. 424/9.6
2003/0044353 A1 * 3/2003 Weissleder et al. ........... 424/9.6
2008/0308744 A1 * 12/2008 Frangioni et al. ............ 250/458.1

OTHER PUBLICATIONS

Weissleder et al. (Nat. Med. 2003, 9, 123-128).*
Konig (J. Microsc. 2000, 200, 83-104).*
Poole et al. (Current Opinion in Ophthalmology 1999, 458-463).*
Hansch, Andreas et al., "Diagnosis of Arthritis Using Near-Infrared Fluorochrome Cy5.5," Investigative Radiology, 2004, vol. 9 No. 10, pp. 626-632, XP008055798.
Chen, Wei-Tsung et al., "Arthritis Imaging Using a Near-Infrared Fluorescence folate-targeted Probe," Arthritis Research and Therapy, 2005, vol. 7 No. 2, pp. R310-R317, XP002355244.
Lai, W-F T et al., "Early Diagnosis of Osteoarthritis Using Cathepsin B Sensitive Near-Infrared Fluorescent Probes," Osteoarthritis and Cartilage, 2004, vol. 12 No. 3, pp. 239-244, United Kingdom, XP002355245.
Wunder, Andreas et al., "In Vivo Imaging of Protease Activity in Arthritis: A Novel Approach for Monitoring Treatment Response," Arthritis and Rheumatism, 2004, vol. 50 No. 8, pp. 2459-2465, XP002355246.
Hansch, A. et al., "In Vivo Imaging of Experimental Arthritis with Near-Infrared Fluorescence," Arthritis and Rheumatism, 2004, vol. 50 No. 3, pp. 961-967, United States, XP002355247.
Paroli, M.P. et al., "Chorioretinopathy and Discoid Plaque-like Lesions of the Eyelids as Useful Indicators of Systemic Lupus Erythematosus (SLE) Progression," Lupus, 2001, vol. 10 No. 8, pp. 571-575, United Kingdom, XP008055809.
Achilefu, S, "Optical Imaging Agents and Potential Application in the Assesment of Pancreatic Beta Cells, " Current Medical Chemistry: Immunology, Endocrine and Metabolic Agents, 2004, vol. 4 No. 4, pp. 253-269, Netherlands, XP008055820.

* cited by examiner

*Primary Examiner*—Michael G Hartley
*Assistant Examiner*—Melissa Perreira
(74) *Attorney, Agent, or Firm*—Miller, White, Zelano, Branigan, P.C.

(57) ABSTRACT

The present invention concerns the use of indocarbocyanine dyes, in particular indotricarbocyanine dyes for the diagnosis of inflammatory diseases, in particular rheumatoid arthritis, methods of diagnosing inflammatory diseases and an apparatus useful to carry out the method of diagnosing.

24 Claims, 3 Drawing Sheets

A

Camera

Excitation fibre with scattering unit and reflector

Support for positioning the hand

B

A

B

C

D

OPTICAL IMAGING OF RHEUMATOID ARTHRITIS

This application claims the benefit of the filing date of U.S. Provisional Application Ser. No. 601694,669 filed Jun. 29, 2005.

The present invention concerns the use of indocarbocyanine dyes, in particular indotricarbocyanine dyes for the diagnosis of inflammatory diseases, in particular rheumatoid arthritis, methods of diagnosing inflammatory diseases and an apparatus useful to carry out the method of diagnosing.

BACKGROUND ART

The indotricarbocyanine dye indocyanine green (ICG, cardiogreen) was first synthesized in the fifties (Heseltine D W (1959) U.S. Pat. No. 2,895,955) and was clinically approved as a diagnostic drug for the assessment of hepatic function and cardiac output, for which ICG exhibits favourable pharmacokinetic properties (Caesar J. et at. (1961) Clin. Sci. 21:43; Dorshow R. B. et al. (1998) J. Biomed. Optics 3:340). In the 1990s it has been discovered as diagnostic imaging agent and is frequently applied for fluorescence angiography to visualize vascular disorders in ophthalmology (Brancato R et al (1998) Semin. Ophthalmol. 13:189; Richard G., Soubrane G., Yanuzzi L. (1998) (eds) Fluorescein and ICG angiography, Thieme, Germany). ICG has been studied as potential NIR contrast agent for the detection of tumors both in animals (Reynolds J S et al. (1999) Photochem. Photobiol. 70:87; Licha K. et al. (2000) Photochem. Photobiol. 72:392) and patients (Ntziachristos V. et al. (2000) Proc. Nat. Acad. Sci. USA 97:2767). The rapid blood clearance of ICG providing only a short time window for contrast enhanced investigations and the rather poor fluorescence quantum efficiency in physiological environments has initiated attempts to design structurally related agents with improved properties (Landsman M. L. J. et al. (1976) J. Appl. Physiol. 40:575; Licha K. et al. (2000) Photochem. Photobiol. 72:392).

The use of fluorescent dyes for diagnostic imaging has been published in numerous patent applications and scientific papers. These publications have in common that they intend to provide improved diagnostic agents and/or agents utilizing structures such as ICG as part of novel chemical polymeric, particular, targeting and/or activatable entities (WO2005/019247, WO2004/028449, US2004/156785, WO2002/087498, WO2002/000265, US2002103517, WO 98/48846). ICG has also been described as a dye for the treatment of diseases using light irradiation (U.S. Pat. No. 6,443,976; Tuchin V. V. et al. (2003) Lasers Surg. Med. 33:296; Greenwell T. J. et al. (2001) Eur. J. Surg. Oncol. 27:368).

US2004156785 describes bioactivatable contrast agents (MRI and optical) comprising ICG and their use in imaging.

The diagnostic imaging of rheumatoid arthritis using light is a known experimental approach (Scheel A. K. et al. (2002) Arthrit. Rheum. 46:1177). The application of fluorescent dyes as imaging probes has been described in the literature using different types of agents (Chen W T et al. (2005) Arthritis Res. Ther. 7:R310; Hansch A. et al. (2004) Invest Radiol 39:626; Wunder A. et al. (2004) Arthritis Rheum. 50:2459). However, none of these publications described the particular suitability of indocarbocyanine dyes, in particular of ICG as diagnostic imaging agent for imaging of inflammatory diseases, in particular of rheumatoid arthritis.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Surprisingly, the present inventors have found a novel approach which allows detecting and quantifying areas of inflammatory disease, in particular rheumatoid arthritis, e.g. in joints, which is based on the differentially distribution and/or resident time of indocarbocyanine dyes, in particular indotricarbocyanine dyes, preferably ICG in healthy and inflamed areas. A time gated equipment for continuous imaging (down to one frame per second) of, e.g. inflamed hands or feet has been developed. Indocarbocyanine near infrared (NR) dyes with pharmacokinetic properties similar to ICG are well suited to identify inflammatory areas, in particular of rheumatoid arthritis in joints. We have developed an algorithm for the investigation of regions of interest in frames and for investigation of fluorescence intensities in dependence on time after i.v. application of, e.g. the indotricarbocyanine dye ICG.

A first aspect of the present invention concerns the use of indocarbocyanine dyes, in particular of indotricarbocyanine dyes for the manufacture of a medicament for the diagnosis of inflammatory diseases.

It has been observed that indocarbocyanines show a preferential localization to and/or alternate distribution in inflammatory regions, if compared to healthy tissue. This preference does not appear to depend on the attachment of a targeting moiety, which might have an increased affinity towards an inflammatory site. Thus, in a preferred embodiment of the present invention no targeting moiety is attached to the indocarbocyanine dye, preferably indotricarbocyanine dye, in particular ICG or analogs thereof, usable according to the present invention.

In a preferred embodiment of the use of the present invention the indocarbocyanine dye has the general formula (I)

(I)

[Chemical structure of formula (I): benzazole with substituents C=A, Y, R³, N⁺–R¹]

wherein C stands for a radical (II) or (III)

(II)

[Chemical structure of formula (II)]

(III)

[Chemical structure of formula (III)]

wherein the position that is labeled with the star means the point of linkage with radical A and wherein A stands for a group selected from the groups (IV), (V), (VI), (VII), or (VIII)

(IV)

[Structure IV]

(V)

[Structure V]

(VI)

[Structure VI]

(VII)

[Structure VII]

(VIII)

[Structure VIII]

wherein
$R^1$ and $R^2$, independently of one another, stand for a $C_1$-$C_4$-sulfoalkyl chain, e.g. sulfomethyl, sulfoethyl, n-sulfopropyl, iso-sulfopropyl, sulfobutyl, iso-sulfobutyl, sec-sulfobutyl, tert-isobutyl; or a saturated or unsaturated, branched or straight-chain $C_1$-$C_{50}$-alkyl chain, e.g. $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{23}$, $C_{13}H_{27}$, $C_{14}H_{19}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, $C_{30}H_{61}$, $C_{31}H_{63}$, which optionally is substituted by 0 to 15, e.g. 1, 2, 3, 4, 5, 6, 7, 8, 9, 10, 11, 12, 13, 14, or 15, oxygen atoms and/or by 0 to 3 carbonyl groups, e.g. 1, 2, or 3, and/or with 0 to 5, e.g. 1, 2, 3, 4, 5, hydroxyl groups or is optionally interrupted by 0 to 15, e.g. 1, 2, 3, 4, 5, 6, 7, 8, 9, 10, 11, 12, 13, 14, or 15, oxygen atoms and/or by 0 to 3. e.g. 1, 2, or 3, carbonyl groups and/or can be substituted with 0 to 5, e.g. 1, 2, 3, 4, or 5, hydroxyl groups;

$R^3$ stands for a straight-chain carbohydrate chain with up to 20 carbon residues, in particular methyl, ethyl, propyl, iso-propyl, butyl, iso-butyl, tert-butyl, pentyl, hexyl, pentyl, octyl, nonyl, decyl, undecyl, dodecyl, tridecyl, tetradecyl, pentadecyl, hexadecyl, heptadecyl, octadecyl, nonadecyl, eicosyl, which is substituted with one or more —OH, —COOH, —SO₃ groups and/or optionally interrupted one or more times (preferably 2, 3, 4, 5 or 6 times) by —O—, —S—, —CO—, —CS—, —CONH, —NHCO—, NHC-SNH—, —SO₂—, —PO₄⁻—, -aryl- and/or —NH— group;

$R^4$ stands for the group —COOE¹, —CONE¹E², —NH-COE¹, —NHCONHE¹, —NE¹E², —OE¹, —OSO₃E¹, —SO₃E¹, —SO₂NHE¹ or -E¹, wherein $E^1$ and $E^2$, independently of one another, stand for a hydrogen atom, a $C_1$-$C_4$-sulfoalkyl chain, e.g. sulfomethyl, sulfoethyl, n-sulfopropyl, iso-sulfopropyl, sulfobutyl, iso-sulfobutyl, sec-sulfobutyl, tert-isobutyl; a saturated or unsaturated, branched or straight-chain $C_1$-$C_{50}$-alkyl chain, e.g. $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_1H_{23}$, $C_{12}H_{23}$, $C_{13}H_{27}$, $C_{14}H_{19}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, $C_{30}H_{61}$, $C_{31}H_{63}$, which optionally is interrupted by 0 to 15 oxygen atoms, e.g. 1, 2, 3, 4, 5, 6, 7, 8, 9, 10, 11, 12, 13, 14, or 15, and/or by 0 to 3 carbonyl groups, e.g. 1, 2, or 3, and/or is substituted with 0 to 5 hydroxyl groups, e.g. 1, 2, 3, 4, or 5;

$R^5$ stands for a hydrogen atom, or a fluorine, chlorine, bromine or iodine atom, methyl, ethyl, propyl or iso-propyl;

b means the number 2 or 3; and

X and Y, independently of one another, stand for O, S, =C(CH₃)₂ or —(CH=CH)—, as well as pharmaceutically acceptable salts and solvates of these compounds. In a preferred embodiment of the use of the present invention the indocarbocyanine dye is a indotricarbocyanine dye, i.e. the group connection a radical according to formula (I) with a radical according to formula (II) or (III) is selected from a structure according to formula (VII) or (VIII).

In a preferred embodiment of the use of the present invention the indotricarboycanine dye is selected from the group consisting of Cy7, indocyanine green (ICG), analogs of ICG, and indotricarbocyanine (ITC). ICG has a structure according to formula (IX):

(IX)

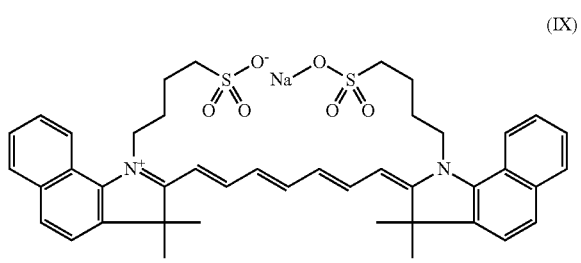

Analogs of ICG are modifications of the structure according to formula (IX), wherein one or more substituents, preferably 1, 2, 3, 4, 5, 6, 7, 8, 9, 10 or more substituens selected from the group consisting of $C_1$-$C_4$-sulfoalkyl chain, e.g. sulfomethyl, sulfoethyl, n-sulfopropyl, iso-sulfopropyl, sulfobutyl, iso-sulfobutyl, sec-sulfobutyl, tert-isobutyl; or a saturated or unsaturated, branched or straight-chain $C_1$-$C_{50}$-alkyl chain, e.g. $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{23}$, $C_{13}H_{27}$, $C_{14}H_{19}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, $C_{30}H_{61}$, $C_{31}H_{63}$, which optionally is substituted by 0 to 15, e.g. 1, 2, 3, 4, 5, 6, 7, 8, 9, 10, 11, 12, 13, 14, or 15, oxygen atoms and/or by 0 to 3 carbonyl groups, e.g. 1, 2, or 3, and/or with 0 to 5, e.g. 1, 2, 3, 4, 5, hydroxyl groups or is optionally interrupted by 0 to 15, e.g. 1, 2, 3, 4, 5, 6, 7, 8, 9, 10, 11, 12, 13, 14, or 15, oxygen atoms and/or by 0 to 3. e.g. 1, 2, or 3, carbonyl groups and/or can be substituted with 0 to 5, e.g. 1, 2, 3, 4, or 5, hydroxyl groups; halogens, e.g. F, Cl, Br, or I are bound to the structure, e.g. by replacing a hydrogen atom. These one or more substitutents are preferably attached to the aromatic system (the ring systems and/or the alkenyl chain connecting the ring structures) and even more preferably at positions corresponding to positions R1, R2, R3 or R4 in structures (I), (II) or (III) above. In addition analogs of ICG within the meaning of this invention show a pharmacokinetic similar to ICG. The pharmacokinetic profile of a substance can be tested by various art known methods. However, it is preferred that the pharmacokinetic of the ICG analog is determined by a test as outlined below in the experimental section, e.g. the distribution kinetics of the ICG analog in a part of the body of a patient with a confirmed diagnosis of an inflammatory disease, preferably rheumatoid arthritis, is determined by, e.g. bolus application of the dye in the vicinity of the part of the body affected with the inflammatory disease, irradiation of the region or part of the region with NIR, measurement of fluorescence at multiple time points. An ICG analog within the meaning of the present invention will show for a given inflammatory disease, in particular arthritis, preferably rheumatoid arthritis, a similar pharmacokinetic as ICG. The pharmacokinetic is similar, if e.g. the time point of maximum accumulation of the ICG analog, i.e. maximum fluorescence intensity, in the inflamed region after a bolus injection of the dye is within at least 500 s, 450 s 400 s, 350 s, 300 s, 250 s, 200 s, preferably 190 s, more preferably at least 180 s, 170 s, 160 s, 150 s, 140 s, 130 s, 120 s, 110 s, 100 s, 90 s, 80 s, 70 s, 60 s, 50 s, 40 s, 30 s, 25, s, 20 s, 15 s, 10 s, 5, s or less of the time point of maximum accumulation of ICG in the same patient or a patient affected by a similar disease. It is understood by someone of skill in the art, that it is necessary for such a comparison of the time points of maximal accumulation in a diseased region between ICG and a potential ICG analog to perform the experiments under almost identical conditions, i.e. administering the same molar amount of ICG and of the ICG analog in the same volume of the same buffer, preferably to the same patient into the same vein etc. The distribution kinetic of the ICG analog in a diseased region can be compared with the distribution kinetics of the same ICG analog in a comparable region of a healthy person. The ICG analog preferably also has a pharmacokinetic in healthy persons similar to ICG. In that respect the term "similar pharmacokinetic" has the meaning as outlined above. The particular suitability of ICG for the detection of inflammatory diseases, in particular rheumatoid arthritis is based on the fact that a rapid accumulation of ICG in diseased areas, in particular in diseased joints is observed while the accumulation of ICG in the joints of healthy patients is slower and does not reach the same maximum fluorescence intensity. Thus, both the difference in the time points of maximal fluorescence and the difference in fluorescence intensity observed between healthy and diseased subjects allow the differentiation between the two situation and, accordingly, the diagnosis.

An inflammatory disease within the meaning of the present invention is a disease characterized by infiltration of macrophages into affected tissue, in particular joints, and veins, the presence of increased amounts of cytokines and/or the presence of increased amounts of T cells. In a preferred embodiment of the use of the present invention the inflammatory disease is selected from the group consisting of arthritis, inflammatory bowel disease, septic shock, osteoporosis, neuropathic pain, viral infection, bacterial infection, insulin-dependent diabetes, non-insulin dependent diabetes, periodontal disease, restenosis, alopecia areta, psoriasis, acute pancreatitis, allograft rejection, allergies, allergic inflammation in the lung, atherosclerosis, multiple sclerosis, cachexia, Alzheimer's disease, stroke, Crohn's disease, inflammatory bowel disease, ischemia, congestive heart failure, pulmonary fibrosis, hepatitis, Guillain-Barre Syndrome, and systemic lupus erythematosus.

In a preferred embodiment of the use of the present invention the arthritis is selected from the group consisting of rheumatoid arthritis, osteoarthritis, psoriatic arthritis, traumatic arthritis, bacterial arthritis (e.g. by streptococcus), post-infectious arthritis, lyme disease (Borreliose), ankylosing spondylitis and rubella arthritis.

Because of the sensitivity of the use of the present invention its use is particular preferred for the diagnosis of early stages of the respective diseases. Such an early diagnosis is particularly desired for arthritic diseases, in particular rheumatoid arthritis, which has a worldwide distribution with an estimated prevalence of 1 to 2%. Prevalence increases with age, approaching 5% in women over age 55. The average annual incidence in the United States is about 70 per 100,000 annually. Both incidence and prevalence of rheumatoid arthritis are two to three times greater in women than in men. Although rheumatoid arthritis may present at any age, patients most commonly are first affected in the third to sixth decades. It is believed that early onset of treatment of rheumatoid arthritis can slow down or prevent progression to full fledged rheumatoid arthritis. The diagnosis of arthritis, in particular rheumatoid arthritis at an early stage, i.e. when the clinical symptoms of, e.g. swelling of joints or pain is not yet present is a particular preferred use of the present invention.

Administration of the indocarbocyanine dye, in particular ICG or an analog thereof may be accomplished by arterial or venous injection or injections into the tissue or joint, which is suspected of being affected with a disease caused or associated with inflammatory processes. For NIR imaging the dyes are preferably administered as an intravenous (IV) bolus. If the dye is administered by bolus injection the injection is preferably administered into a vessel in the vicinity of the region to be diagnosed, which will transport the dye into the region. The skilled person is capable of selecting a blood vessel suitable for administration of the dye. Typically, the patient is fasted at least 4 hours prior to administration of the dye.

In a preferred embodiment of the use of the present invention the diagnostic dye is administered in an amount of 10 mg/kg body weight or less, 9 mg/kg body weight or less, 8 mg/kg body weight or less, 7 mg/kg body weight or less, 6 mg/kg body weight or less, 5 mg/kg body weight or less, 4 mg/kg body weight or less, 3 mg/kg body weight or less, 2 mg/kg body weight or less, preferably 1 mg/kg body weight or less, 0.9 mg/kg body weight or less, 0.8 mg/kg body weight or less, 0.7 mg/kg body weight or less, 0.6 mg/kg body weight or less, 0.5 mg/kg body weight or less, 0.4 mg/kg body weight or less, 0.3 mg/kg body weight or less, 0,2 mg/kg body weight or less, most preferably in an amount of 0.1 mg/kg body weight or less.

The dye is preferably administered in combination with a pharmaceutically acceptable carrier, to the subject. As used herein, a pharmaceutically acceptable carrier may include any and all solvents, dispersion media, antibacterial and antifungal agents, isotonic agents, and the like. The use of such media and agents for pharmaceutically active substances is well known in the art.

The dye is preferably formulated as a sterile, pyrogen-free, parenterally acceptable aqueous solution. The preparation of such parenterally acceptable solutions, having due regard to pH, isotonicity, stability, and the like, is within the skill in the art.

The term "pharmaceutically acceptable salt" refers to a salt of the dye. Suitable pharmaceutically acceptable salts of dyes useable according to the present invention include acid addition salts which may, for example, be formed by mixing a solution of a dye with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the dye carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counter-anions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like.

In a further aspect the present invention is directed at a method of diagnosing an inflammatory disease comprising the following steps:
(a) administering an indocarbocyanine dye, in particular an indotricarbocyanine dye, preferably by bolus injection,
(b) exposing a region of the body to light of a wavelength capable to excite the indotricarbocyanine dye,
(c) measuring the fluorescence in the region of the body at multiple time points.

In a preferred embodiment of the method of the present invention the indocarbocyanine dye has the general formula (I)

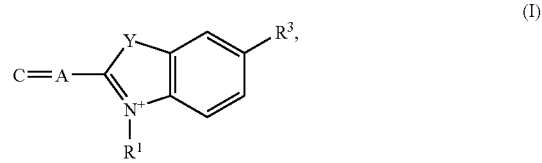

wherein C stands for a radical (II) or (III)

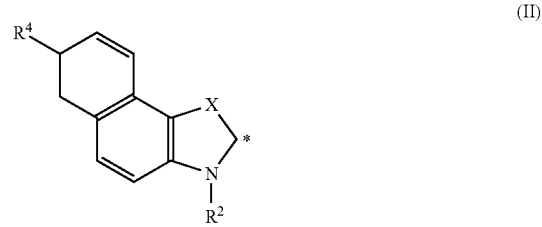

wherein the position that is labeled with the star means the point of linkage with radical A and wherein A stands for a group selected from the groups (IV), (V), (VI), (VII), or (VIII)

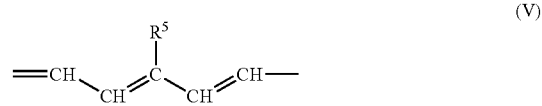

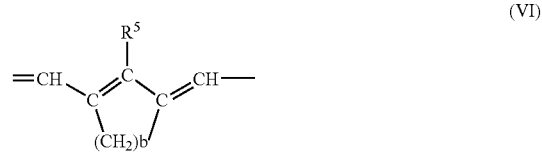

-continued

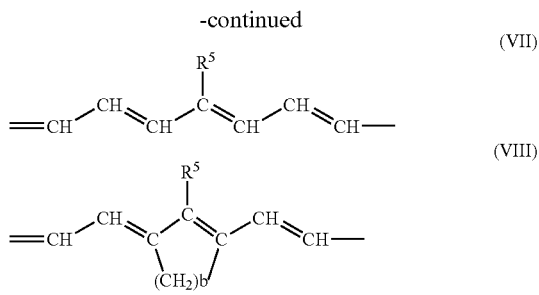

wherein $R^1$ and $R^2$, independently of one another, stand for a $C_1$-$C_4$-sulfoalkyl chain, e.g. sulfomethyl, sulfoethyl, n-sulfopropyl, iso-sulfopropyl, sulfobutyl, iso-sulfobutyl, sec-sulfobutyl, tert-isobutyl; or a saturated or unsaturated, branched or straight-chain $C_1$-$C_{50}$-alkyl chain, e.g. $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{23}$, $C_{13}H_{27}$, $C_{14}H_{19}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, $C_{30}H_{61}$, $C_{31}H_{63}$, which optionally is substituted by 0 to 15, e.g. 1, 2, 3, 4, 5, 6, 7, 8, 9, 10, 11, 12, 13, 14, or 15, oxygen atoms and/or by 0 to 3 carbonyl groups, e.g. 1, 2, or 3, and/or with 0 to 5, e.g. 1, 2, 3, 4, 5, hydroxyl groups or is optionally interrupted by 0 to 15, e.g. 1, 2, 3, 4, 5, 6, 7, 8, 9, 10, 11, 12, 13, 14, or 15, oxygen atoms and/or by 0 to 3. e.g. 1, 2, or 3, carbonyl groups and/or can be substituted with 0 to 5, e.g. 1, 2, 3, 4, or 5, hydroxyl groups;

$R^3$ stands for a straight-chain carbohydrate chain with up to 20 carbon residues, in particular methyl, ethyl, propyl, iso-propyl, butyl, iso-butyl, tert-butyl, pentyl, hexyl, pentyl, octyl, nonyl, decyl, undecyl, dodecyl, tridecyl, tetradecyl, pentadecyl, hexadecyl, heptadecyl, octadecyl, nonadecyl, eicosyl, which is substituted with one or more —OH, —COOH, —SO$_3$ groups and/or optionally interrupted one or more times (preferably 2, 3, 4, 5 or 6 times) by —O—, —S—, —CO—, —CS—, —CONH, —NHCO—, NHC-SNH—, —SO$_2$—, —PO$_4^-$—, -aryl- and/or —NH— group;

$R^4$ stands for the group —COOE$^1$, —CONE$^1$E$^2$, —NH-COE$^1$, —NHCONHE$^1$, —NE$^1$E$^2$, —OE$^1$, —OSO$_3$E$^1$, —SO$_3$E$^1$, —SO$_2$NHE$^1$ or -E$^1$, wherein E$^1$ and E$^2$, independently of one another, stand for a hydrogen atom, a $C_1$-$C_4$-sulfoalkyl chain, e.g. sulfomethyl, sulfoethyl, n-sulfopropyl, iso-sulfopropyl, sulfobutyl, iso-sulfobutyl, sec-sulfobutyl, tert-isobutyl; a saturated or unsaturated, branched or straight-chain $C_1$-$C_{50}$-alkyl chain, e.g. $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{23}$, $C_{13}H_{27}$, $C_{14}H_{19}$, $C_{15}H_{31}$, $C_{16}H_{33}$, $C_{17}H_{35}$, $C_{18}H_{37}$, $C_{19}H_{39}$, $C_{20}H_{41}$, $C_{21}H_{43}$, $C_{22}H_{45}$, $C_{23}H_{47}$, $C_{24}H_{49}$, $C_{25}H_{51}$, $C_{26}H_{53}$, $C_{27}H_{55}$, $C_{28}H_{57}$, $C_{29}H_{59}$, $C_{30}H_{61}$, $C_{31}H_{63}$, which optionally is interrupted by 0 to 15 oxygen atoms, e.g. 1, 2, 3, 4, 5, 6, 7, 8, 9, 10, 11, 12, 13, 14, or 15, and/or by 0 to 3 carbonyl groups, e.g. 1, 2, or 3, and/or is substituted with 0 to 5 hydroxyl groups, e.g. 1, 2, 3, 4, or 5;

$R^5$ stands for a hydrogen atom, or a fluorine, chlorine, bromine or iodine atom, methyl, ethyl, propyl or iso-propyl;

b means the number 2 or 3; and

X and Y, independently of one another, stand for O, S, =C(CH$_3$)$_2$ or —(CH=CH)—, as well as pharmaceutically acceptable salts and solvates of these compounds.

In a preferred embodiment of the use of the present invention the indocarbocyanine dye is a indotricarbocyanine dye, i.e. the group connection a radical according to formula (I) with a radical according to formula (II) or (III) is selected from a structure according to formula (VII) or (VIII).

In a preferred embodiment of the method of the present invention the indotricarboycanine dye is selected from the group consisting of Cy7, indocyanine green (ICG), analogs of ICG, and indotricarbocyanine (ITC). In this context the term "ICG analog" has the meaning as outlined above.

In a preferred embodiment of the method of the present invention the inflammatory disease is selected from the group consisting of arthritis, inflammatory bowel disease, septic shock, osteoporosis, neuropathic pain, viral infection, bacterial infection, insulin-dependent diabetes, non-insulin dependent diabetes, periodontal disease, restenosis, alopecia areta, psoriasis, acute pancreatitis, allograft rejection, allergies, allergic inflammation in the lung, atherosclerosis, multiple sclerosis, cachexia, Alzheimer's disease, stroke, Crohn's disease, inflammatory bowel disease, ischemia, congestive heart failure, pulmonary fibrosis, hepatitis, Guillain-Barre Syndrome, and systemic lupus erythematosus.

In a preferred embodiment of the method of the present invention the arthritis is selected from the group consisting of rheumatoid arthritis, osteoarthritis, psoriatic arthritis, traumatic arthritis, bacterial arthritis (e.g. by streptococcus), post-infectious arthritis, lyme disease (Borreliose), ankylosing spondyliitis and rubella arthritis, in particular rheumatoid arthritis.

Because of the sensitivity of the method of the present invention it is preferred for the diagnosis of early stages of the respective diseases. The diagnosis of arthritis, in particular rheumatoid arthritis at an early stage, i.e. when the clinical symptoms of, e.g. swelling of joints or pain is not yet present is particular preferred.

In a preferred embodiment of the method of the present invention the diagnostic is administered in an amount of 10 mg/kg body weight or less, 9 mg/kg body weight or less, 8 mg/kg body weight or less, 7 mg/kg body weight or less, 6 mg/kg body weight or less, 5 mg/kg body weight or less, 4 mg/kg body weight or less, 3 mg/kg body weight or less, 2 mg/kg body weight or less, preferably 1 mg/kg body weight or less, 0.9 mg/kg body weight or less, 0.8 mg/kg body weight or less, 0.7 mg/kg body weight or less, 0.6 mg/kg body weight or less, 0.5 mg/kg body weight or less, 0.4 mg/kg body weight or less, 0.3 mg/kg body weight or less, 0,2 mg/kg body weight or less, most preferably in an amount of 0.1 mg/kg body weight or less.

In a preferred embodiment of the method of the present invention the diagnostic is injected into the region of the body to be diagnosed or into a blood vessel or the lymphatic system, which provides blood or lymph to the region of the body to be diagnosed. In case of imaging of a hand the diagnostic is preferably injected into the vein of the arm.

In a preferred embodiment of the method of the present invention the light in step (b) is applied continuously, amplitude modulated or pulsed. If the light is applied pulsed it is preferred that the measuring is carried out in pulses synchronized with the light pulses, which allows a reduction of background noise due to ambient light. It is preferred that the source of the excitation light is a laser. A preferred type of laser is a Nd:YAG state laser combined with an optical parametric oscillator pumped by the third harmonic. However, other type of lasers which can provide the desired excitation wavelength can equally be employed.

In a preferred embodiment of the method of the present invention the light has a wavelength of between 600 nm and 2.2 µm. Preferably the excitation wavelength is chosen in such that the wavelength is close to the maximum of the absorption maximum of the respectively used NIR dye. A particular preferred range to choose the excitation wavelength is between 700 nm and 900 nm. For ICG the absorption maximum is at a wavelength of about 780 nm, accordingly, it is preferred to choose an excitation wavelength of about 780 nm when using ICG.

For the imaging of inflammatory processes, in particular in the joints of the hand it has been shown that the difference in fluorescence pattern between healthy and diseased subjects is most prominent within a short time frame after administration of the NIR dye. Thus, in a preferred embodiment of the method of the present invention the fluorescence is measured at multiple time points at least for 20 s, preferably at least for 30 s, 40 s, 50 s, 60 s, 70 s, 80 s, 90 s, 100 s, 110 s, 120 s, 130 s, 140 s, 150 s, 180 s, 190 s, 200 s, 210 s, 220, 230 s, 240 s, 250 s, 260 s, 270 s, 280 s, 290 s, or at least 300 s after administration of the indocarbocyanine dye, preferably indotricarbocyanine, more preferably ICG or analog thereof. The pharmacokinetic An early distribution of the indocarbocyanine, in particular indotricarbocyanine to the regions suspected of inflammation will be indicative of an inflammatory process. The maximum of fluorescence in the regions suspected of disease, e.g. one or more joints in arthritis and areas of the skin in psoriasis, will preferably be reached within 10 s, preferably 20 s, 25 s, 30 s, 35 s, 40 s, 45 s, 50 s, 55 s, 60 s, 65 s, 70 s, 75 s, 80 s, 90 s, 100 s, 10 s, 120 s, 130 s, 140 s, 150 s, 160 s, 170 s, or 180 s. Such an early maximum in the are suspected of disease is indicative an inflammatory process. For the diagnosis of arthritis, in particular rheumatoid arthritis a maximum of fluorescence in one or more of the joints examined within a range of 20 s to 150 s, preferably 30 s to 100 s after administration of the dye is indicative of disease, while a later maximum is indicative of a healthy subject. In addition the maximal fluorescence observed in areas of disease is typically higher than the maximal fluorescence observed in the same unaffected areas, accordingly, a low level of fluorescence at any time point after the administration of the indocarbocyanine dye can also be indicative of disease. In that respect a low level is a level, which is at least 70%, preferably 60%, more preferably 50%, or less than that observed in diseased areas. The skilled person can based on the teaching in this specification can establish appropriate time ranges, wherein the detection of a fluorescence maximum is indicative of disease.

In a preferred embodiment of the method of the present invention fluorescence in the region of the body is detected at each time point as one image and/or by scanning the region of the body. If a whole or part image of the body region is detected it is preferred to use a camera for this purpose. Suitable cameras are known in the art and comprise, e.g. CCD and CMOS cameras. If a larger image of the region of the body to be diagnosed for the presence of an inflammatory disease is recorded it is possible to define certain subregions within this image, which are used for determination of pharmacokinetic of the respective dye. For example, when diagnosing inflammatory diseases known to affect primarily the joints the field of view of the image of the body part recorded will usually comprise areas known not to be affected by the inflammatory disease. One or more subregions will then be defined in the field of view in those areas where, e.g. the joints are located.

The distribution and/or retention of the fluorescent dye over time allows to identify areas of inflammation, in particular of rheumatoid arthritis. Since the altered distribution and/or retention of the administered dye indicative of inflammation is only a relatively short lived transient phenomenon in a preferred embodiment of the method of the present invention the fluorescence is detected in intervals of 15 s or less, 10 s or less, 9 s or less, 8 s or less, 7 s or less, 6 s or less, 5 s or less, 4 s or less or 3 s or less, 2 s or less or 1 s or less.

In a preferred embodiment of the method of the present invention a fluorescent standard is provided on or in the vicinity of the imaged body region to normalize the measured fluorescence. Preferably such a fluorescent standard is a structure, e.g. a plastic disc, wherein the respective NIR dye used in the examination is immobilized.

In a preferred embodiment of the method of the present invention a computer program is used to determine a time resolved pattern of circulation, preferably a pattern of blood circulation within the region of the body to be examined. To that end images at multiple time points are acquired. The term "multiple time points" as used in the present invention refers to at least 2 time point, i.e. at least two images, preferably at least 3, 4, 5, 6, 7, 8, 9, 10, 11, 12, 13, 14, 15, 16, 17, 18, 19, 20, 25, 30, 35, 40, 45, 50 time points, i.e. images, which are preferably taken in above outlined preferred intervals.

In a preferred embodiment of the method of the present invention the pattern of blood circulation in a patient suspected of having an inflammatory disease is compared to the pattern of blood circulation in a healthy patient and wherein alterations of the pattern of blood circulation are indicative of inflammatory disease. In that sense alteration of the pattern of blood circulation comprises extended resident times of the NIR dyes, changes of flow patterns or an altered temporal distribution.

In a preferred embodiment of the method of the present invention the region of the body is selected from hand, foot, knee, elbow and shoulder.

In a preferred embodiment of the method of the present invention an increase of fluorescence at, e.g. the joints is indicative of an inflammatory disease, e.g. rheumatoid arthritis. Preferably, such increase is detected within less than 300 s, less than 290, 280, 270, 260, 250, 240, 230, 220, 210, 200, 190, 170, 160, 150, 140, 130, 120, 110, 100, 90, 95, 90, 85, 80, 75, 70, 65, 60, 55, 50, 45, 40, 35, 30 or less than 25 s after administration of the indocarbocyanine dye, in particular indotricarbocyanine dye.

In a preferred embodiment of the method of the present invention the indocarbocyanine dye, in particular indotricarbocyanine is chosen in such that the wavelength of excitation maximum differs from the wavelength of the fluorescence maximum by at least 10 nm, preferably at least 20 nm, more preferably at least 30 nm, more preferably at least 35 nm, more preferably at least 40 nm.

In a further aspect the present invention is directed at a device for carrying out a method of the present invention, wherein the light source is a laser, preferably a pulsed or continuous laser. Suitable lasers are known in the art and comprise among others Nd-YAG lasers. The laser is preferably connected to a fibre, which can serve at least two purposes, firstly, it directs the laser light towards the examination area and, secondly, it can provide a mixing of modes of the light used for illumination. The end of the laser can be provided with a suitable optic to homogenously illuminate the examination area. Preferably such an optic has a lens assembly or is a scattering sphere connected to the end of the fibre. In the later case the fibre is preferably fitted with a reflector to prevent illumination outside the area of examination.

In a preferred embodiment of the device of the present invention the fluorescence is detected in a transmission and/or reflexion assembly.

In a preferred embodiment of the device of the present invention the device comprises a long pass filter, which suppresses the excitation wavelength by at least OD 7.

In a preferred embodiment of the device of the present invention the device is a camera, if a plane of the body region is irradiated or the device has a scanning spot detector, if spots of the body region are irradiated.

In a preferred embodiment of the device of the present invention the change of the indocarbocyanine dye, in particular indotricarbocyanine dye within the body region.

This invention is particularly concerned with the use of indocarbocyanine dye, in particular indotricarbocyanine dyes in particular of ICG for the detection of rheumatoid arthritis. It is also concerned with a method for detection a NIR dye, preferably injected into the body with a bolus injection, by optical excitation and detection of the emitted fluorescence. This method is further characterized in that a fluorescent dye is administered, light of a suitable wave length is radiated onto and into the body and the location dependent variation of fluorescence intensity is measured. This invention is further concerned with a method characterized in that the excitation light is emitted as a pulse or as a continuous radiation.

A further aspect is a method characterized in that the distribution of the emitted fluorescence is depicted by way of fast acquisition of frames of a series of pictures. Changes of the flow pattern of blood due to disease are visualized by, for example an altered temporal distribution or, for example, by an extended resident time of the dye in the respective body region, e.g. digits of the hand. A standard method for detecting inflammatory rheumatoid diseases by way of bolus injection of contrast agents is nuclear resonance tomography using gadolinium diethylene triamine pentaacetic acid (Gd-GTPA). A further known method is positron emission tomography (PET) wherein radioisotopes are used as contrast agents. Because of the space requirements and the costs associated with both of these methods, they can not be employed for the general screening of the population to allow early detection of inflammatory diseases, in particular early stages of rheumatoid arthritis. However, optical methods like NIR imaging can be realized with compact comparatively cheap devices. One advantage of determining fluorescence is that the fluorescent dye can be detected in the near infrared (NIR) almost without background noise from the tissue since biological tissue does not or only slightly fluoresce within the wavelength that indocarbocyanine dye, preferably indotricarbocyanines, in particular ICG fluoresces in. Excitation and resulting fluorescence light is strongly scattered in the tissue and, thus, only alterations can be visualized which are close to the surface, i.e. not deeper than 10 cm. Thus, to image inflammatory diseases in less accessible areas it is envisioned that endoscopic or similar devices can be used in the context of the method of the present invention. The apparatus depicted in FIG. 1 can be used for visualizing a bolus injection of dye which has been injected into the vein of the arm pit. The fluorescent dye used is ICG which has an absorption maximum at 780 nm and a fluorescence maximum at 820 nm.

This application also concerns a device for registering fluorescent radiation characterized in that the optical radiation source, preferably a laser, which works in pulse or continuous mode is used and that the detection is carried out at a second frequency different from the frequency of the excitation wavelength. In this respect it is preferred that the detection of the fluorescence is carried out in a reflection or transmission arrangement. To suppress the excitation wavelength a long pass filter is used which allows to suppress the excitation wave length preferably by an OD >7. The device according to the invention is further characterized in that the detection of the fluorescence radiation is carried out with a sensitive camera during irradiation of a wider surface area or with a scanned system in applications using spot excitation and spot detection. Furthermore, the device is characterized in that a solid state material with known fluorescence, e.g. a plastic disc comprising the respective NIR dye, is used for the purpose of normalizing the fluorescence radiation. Finally, the device is characterized in that it provides a computer programme, which allows the analysis of the frames in order to provide a normalized presentation of the dynamics of the NIR dye within the determined regions of interest (ROIs).

EXAMPLES

1. Excitation

The excitation of the NIR-dyes is carried out with the help of an optical parametric oscillator which is pumped with the 3. harmonic ($\lambda$=350 nm, $E_{pulse}$=100 mJ) of a Nd:YAG laser. The wave length of the laser radiation of the system is variable and can be varied between 415 nm and 2.2 µm. The energy of the pulse is 5 mJ and the duration of the pulse is 3 ns. The laser beam is coupled into a fibre with a diameter of 600 µm. Due to strong bending of the fibre a good mix of modes is achieved, which leads to homogeneous radiation. Within the imaging area of the intensified CCD camera a circular area of about 220 mm in diameter is illuminated almost homogeneously (corresponds to a radiation of 16 µJ/cm$^2$). The almost homogeneous illumination is achieved by a small scattering sphere at the end of the fibre which is located in a reflector. The excitation wavelength can be selected depending on the photo physical properties of the respectively used dye.

2. Imaging of Fluorescence

A glass long pass filter ($\lambda_{50\%}$=780 nm (colour glass 2 mm) and two interference long pass filters $\lambda_{50\%}$=800 nm) are used to suppress the excitation wavelength. The fluorescence is detected on a photocathode of a water/Peltier cooled intensified CCD camera with a standard lens with a focal length of 35 mm (f=1.4). To suppress ambient light the opening of the iCCD camera is synchronized with the laser pulses. The opening signal to the iCCD camera is an electric pulse with a duration of 10 ns. The exposure time is 0.04 s over 40 accumulations. Accordingly within a period of 3 s it is possible to take 300 exposure frames. An over exposure, i.e. over modulation of the signal, is prevented by selecting appropriate lens aperture. For the preferred fluorescent dye ICG the emitted fluorescence is detected at $\lambda_{obs} \geq 800$ nm.

3. Application of an NIR Dye to a Patient

As a reference during examination a plastic disc of a thickness of 2 mm, which comprises embedded glass beads comprising the respectively used NIR dye, e.g. ICG is provided. This disc is placed at one end of the field of view of the iCCD camera but taking care to keep a distance to the region of the body examined, e.g. for a hand a distance of about to 2 cm is appropriate. The hand to be examined is placed with the back of the hand pointing towards the camera on a preformed support, which optically separates the digits to prevent fluorescent crosstalk. To carry out the measurement about 0.1 mg/kg body weight of the dissolved dye is injected into the vein of the arm. Frames of the iCCD camera are taken in 3 second intervals and the injection of the NIR dye is carried out manually by bolus injection 6 seconds after the gathering of frames was commenced, i.e. the bolus is injected together with the 3. frame. The first 2 frames serve the purpose of determining background fluorescence.

Figure 1:
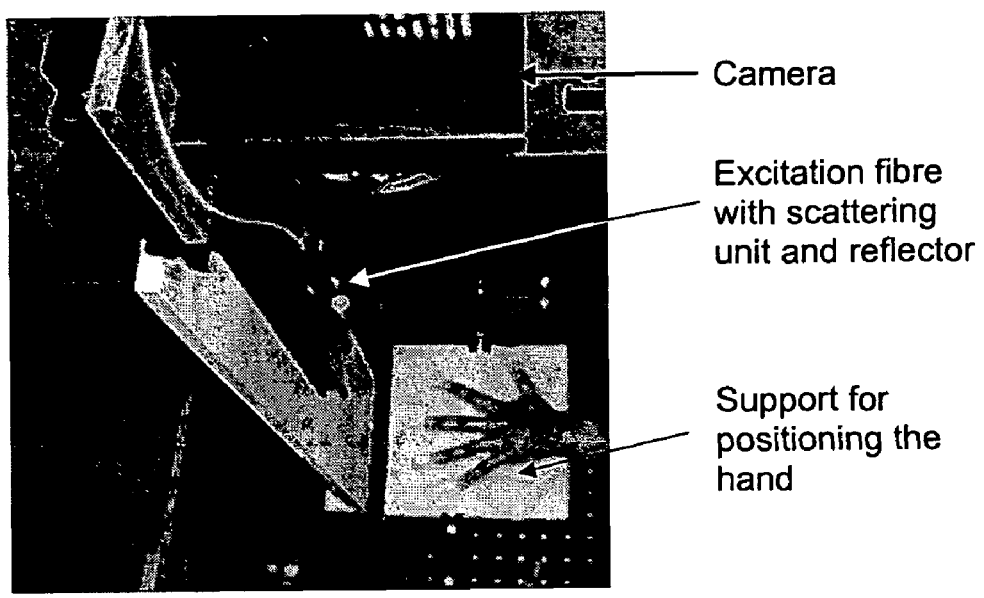
FIG. 1 Panel A is a photographic image of the fluorescence detection apparatus of the present invention including the CCD camera, the fiber and the support for the hand. Panel B schematically depicts the design of the fluorescence detection apparatus of the present invention. OPO stands for optical parametric oscillator, SHG stands for second harmonic generation, THG stands for third harmonic generation, Nd-YAG stands for a pulsed solid-state laser.
Figure 1:
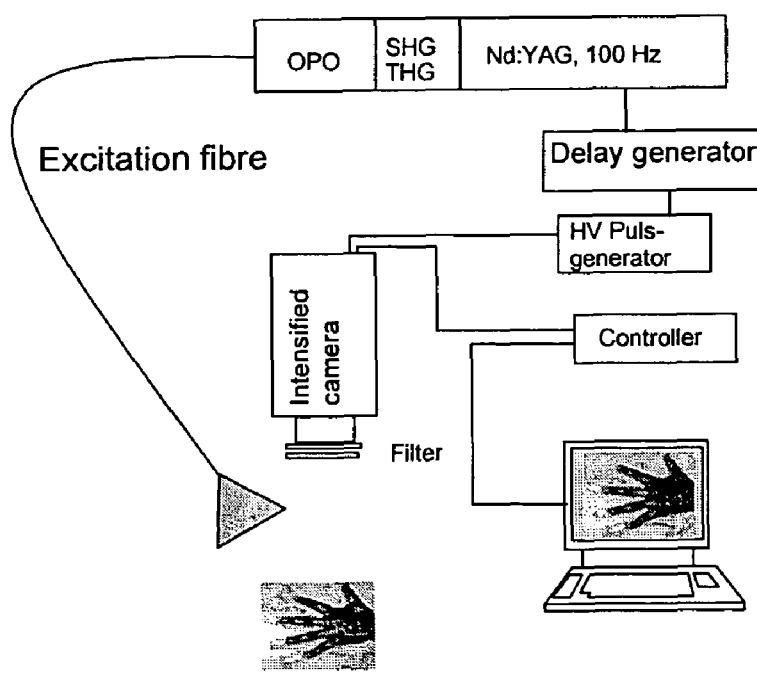
Figure 2:
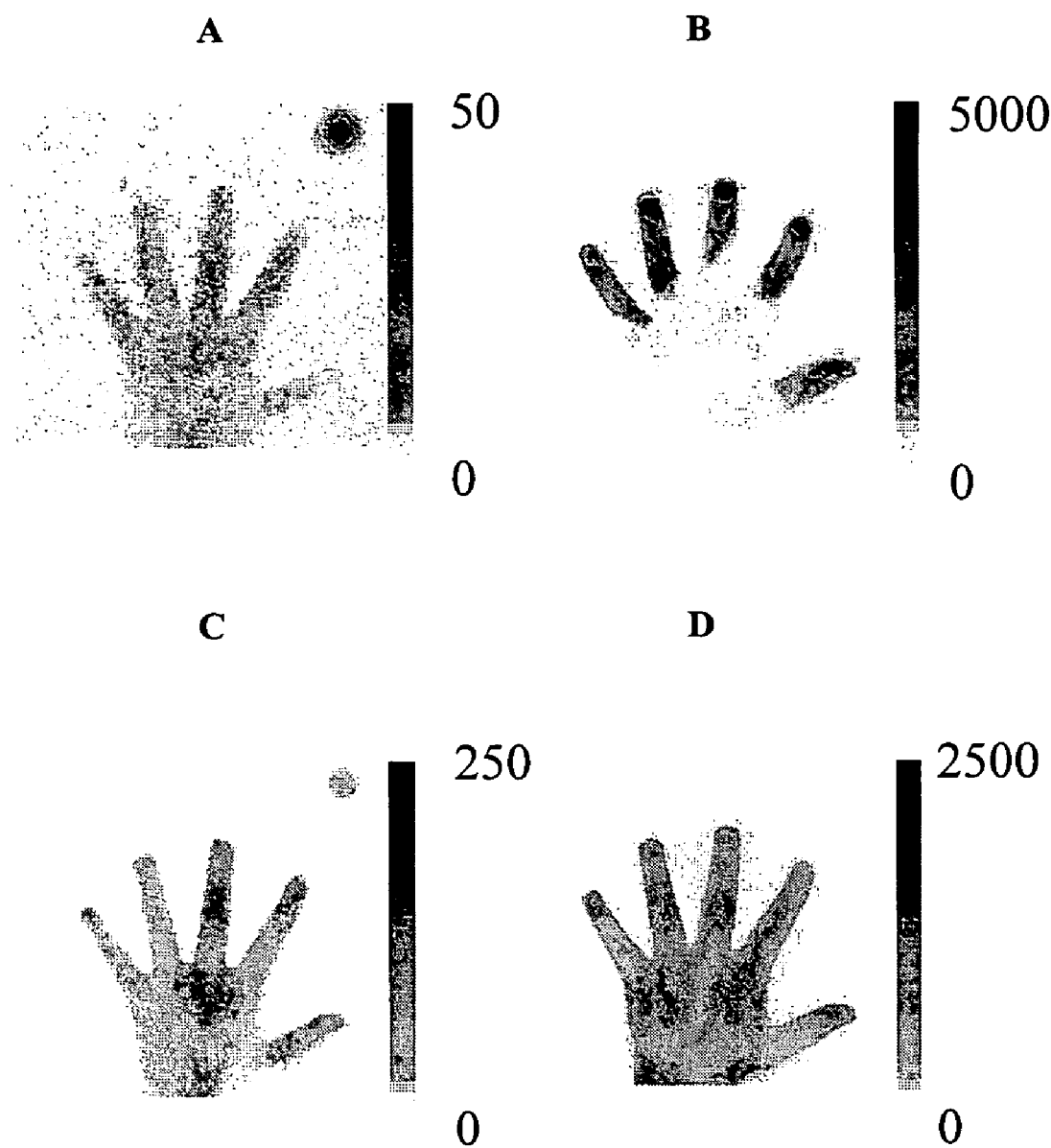
FIG. 2 Depicts the fluorescence pictures of the back of the hand of a healthy subject at different time points. Panel A shows an image taken prior to the administration of the dye. Panel B shows an image 47 s after the administration of 0.1 mg/kg K.G. ICG. Panel C shows an image 1040 s after the administration of ICG. Panel D shows an image 104 s after the administration of ICG. Fluorescence is first detectable in the finger tips.
Figure 3:
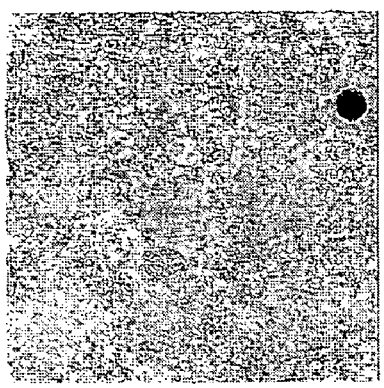
FIG. 3 Depicts the fluorescence pictures of the back of the hand of a patient with rheumatoid arthritis at different time points. Panel A shows an image taken prior to the administration of the dye. Panel B shows an image 45 s after the administration of 0.1 mg/kg K.G. ICG. Panel C shows an image 900 s after the administration of ICG. Panel D shows an image 102 s after the administration of ICG. Fluorescence is first detectable in the joints of the finger.
Figure 3:
Figure 3:
Figure 3:

The fluorescence pattern of healthy volunteers is characterized by strong increase in fluorescence about 40 seconds after injection of a bolus of 0.1 mg/kg B.W. in the fingertips and subsequently in distal and proximal joints (see FIG. 2). This sequence is changed in inflamed limbs (see FIG. 3).

4. Data Processing and Analysis

The detected data (images) are recorded on a computer and saved to disc. For analysis of the fluorescence intensity of the joints so called "regions of interest" (ROIs) are defined within the area of the distal interphalangeal joints (DIP), the proximal interphalangeal joints (PIP) and of the metakarpophalangeal joints (MP) as well as within the reference area. The average mean values covering the ROIs of the joints during the examination serve as fluorescence intensities (mean FI ankle joint). The fluorescence intensities are normalized to the fluorescence intensity of the reference (mean FI reference) (NFI).

NFI=FI ankle joint/FI reference wherein NFI=normalized fluorescence intensity,
FI ankle joint=mean fluorescence intensity over ankle joints and
FI reference=mean fluorescence intensity of the reference.

For the statistic analysis the NFI at defined time points after NIR dye, e.g. ICG, administration is collected and the data for all joints of the hand is determined. Thus, the time course of the fluorescence intensity is determined for the individual joints. The comparison of the joints of a digit of the hand shows characteristic differences in the invasion, i.e. temporal distribution, properties of the dye in patients with inflammatory rheumatoid diseases (see FIG. 3). In healthy subjects the contrast agent is visible first in the tip of the finger (see FIG. 2). In rheumatic patients the inflamed altered joints are first visible (see FIG. 3). The patient has arthritis within the area of MCP II, III of PIP II, III and V as well as an involvement of the carpal bone while sparing the DIP joints. Taken together this is a typical example of a rheumatoid arthritis.

The entire disclosures of all applications, patents and publications, cited herein and of corresponding European application No. 05015365.9, filed Jun. 29, 2005 and U.S. Provisional Application Ser. No. 60/694,669, filed Jul. 14, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for the diagnosis of an inflammatory disease of a joint comprising
   (i) administering to a subject a diagnostically effective amount of
      (a) an indocarbocyanine dye of formula (I)

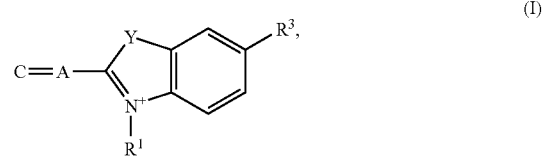

wherein C stands for a radical (II) or (III)

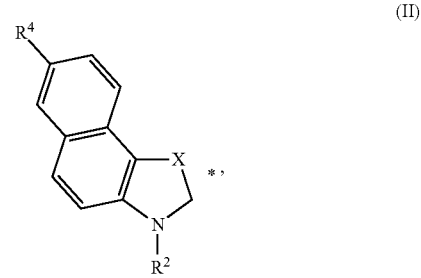

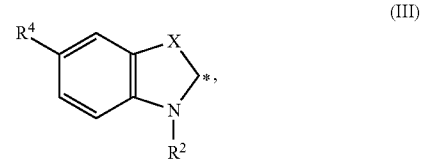

wherein the position that is labelled with the star means the point of linkage with radical A and wherein A stands for a group (IV), (V), (VI), (VII), or (VIII)

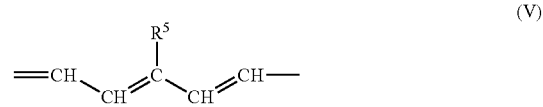

-continued

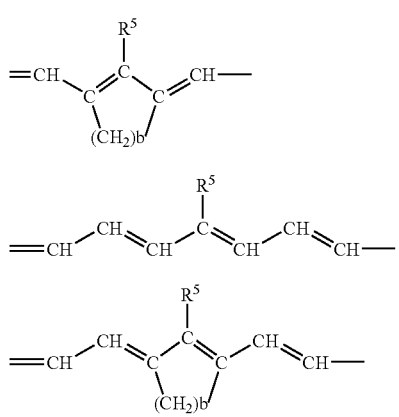

wherein

R¹ and R², independently of one another, stand for a $C_1$-$C_4$-sulfoalkyl chain or a saturated or unsaturated, branched or straight-chain $C_1$-$C_{50}$-alkyl chain, which optionally is substituted by 0 to 15 oxygen atoms and/or by 0 to 3 carbonyl groups and/or with 0 to 5 hydroxyl groups or optionally interrupted by 0 to 15 oxygen atoms and/or by 0 to 3 carbonyl groups and/or can be substituted with 0 to 5 hydroxyl groups;

R³ stands for a straight-chain carbohydrate chain with up to 20 carbon residues, which is substituted with one or more —OH, —COOH, —SO₃ groups and/or optionally interrupted one or more times by —O—, —S—, —CO—, —CS—, —CONH, —NHCO—, NHC-SNH—, —SO₂—, —PO₄³¹—, -aryl- and/or —NH— group;

R⁴ stands for the group —COOE¹, —CONE¹E², —NH-COE¹, —NHCONHE¹, —NE¹E², —OE¹, —OSO₃E¹, —SO₃E¹, —SO₂NHE¹ or -E¹, wherein E¹ and E², independently of one another, stand for a hydrogen atom, a $C_1$-$C_4$-sulfoalkyl chain, a saturated or unsaturated, branched or straight-chain $C_1$-$C_{50}$-alkyl chain, which optionally is interrupted by 0 to 15 oxygen atoms and/or by 0 to 3 carbonyl groups and/or is substituted with 0 to 5 hydroxyl groups;

R⁵ stands for a hydrogen atom, or a fluorine, chlorine, bromine or iodine atom, methyl, ethyl, propyl or isopropyl;

b means the number 2 or 3; and

X and Y, independently of one another, stand for O, S, =C(CH₃)₂ or —(CH=CH)—, or a salt or solvate of thereof or (b) an indocarbocyanine dye which is Cy7, indocyanine green (ICG), an analog of ICG, or indotricarbocyanine (ITC), wherein no targeting moiety is attached to the dye (a) or (b), (ii) exposing the joint to be imaged to light of a wavelength between 700 nm and 900 nm and (iii) measuring fluorescence at multiple time points within 500 seconds after administration of said dye, wherein the distribution of said indocarbocyanine dye in the joint regions suspected of having inflammation is indicative of the presence of inflammatory joint disease.

2. A method according to claim 1, wherein the inflammatory disease is arthritis.

3. A method according to claim 2, wherein the arthritis is selected from the group consisting of rheumatoid arthritis, osteoarthritis, psoriatic arthritis, traumatic arthritis, bacterial arthritis, post-infectious arthritis, lyme disease (Borreliose), ankylosing spondyliitis and rubella arthritis.

4. A method according to claim 1, wherein the indocarbocyanine dye is administered in an amount of 10 mg/kg body weight or less.

5. A method of diagnosing an inflammatory joint disease comprising:

(a) administering to a subject a diagnostically effective amount of an indocarbocyanine dye, by bolus injection (b) exposing a region of the body of said subject to light of a wavelength between 700 nm and 900 nm (c) measuring fluorescence in the region of the body at multiple time points which are less than 500 seconds after administration of said dye, wherein the indocarbocyanine dye has the formula (I)

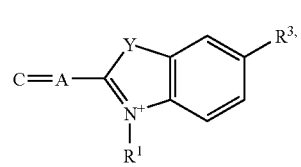

wherein C stands for a radical (II) or (III)

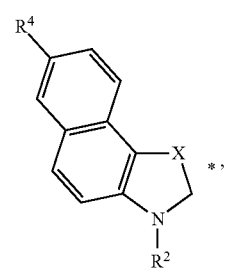

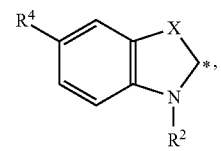

wherein the position that is labelled with the star means the point of linkage with radical A and wherein A stands for a group (IV), (V), (VI), (VII), or (VIII)

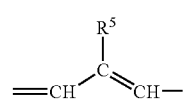

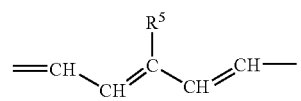

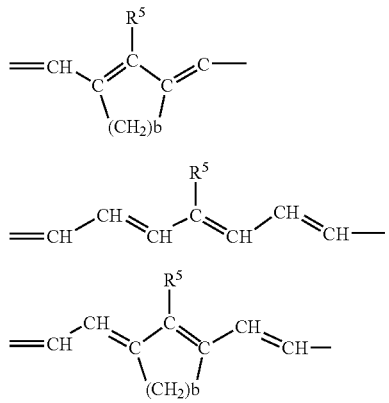

wherein
- $R^1$ and $R^2$, independently of one another, stand for a $C_1$-$C_4$-sulfoalkyl chain or a saturated or unsaturated, branched or straight-chain $C_1$-$C_{50}$-alkyl chain, which optionally is substituted by 0 to 15 oxygen atoms and/or by 0 to 3 carbonyl groups and/or with 0 to 5 hydroxyl groups or optionally interrupted by 0 to 15 oxygen atoms and/or by 0 to 3 carbonyl groups and/or can be substituted with 0 to 5 hydroxyl groups;
- $R^3$ stands for a straight-chain carbohydrate chain with up to 20 carbon residues, which is substituted with one or more —OH, —COOH, —$SO_3$ groups and/or optionally interrupted one or more times by —O—, —S—, —CO—, —CS—, —CONH, —NHCO—, NHCSNH—, —$SO_2$—, —$PO_4^-$—, -aryl- and/or —NH— group;
- $R^4$ stands for the group —$COOE^1$, —$CONE^1E^2$, —NH-$COE^1$, —$NHCONHE^1$, —$NE^1E^2$, —$OE^1$, —$OSO_3E^1$, —$SO_3E^1$, —$SO_2NHE^1$ or -$E^1$, wherein
  - $E^1$ and $E^2$, independently of one another, stand for a hydrogen atom, a $C_1$-$C_4$-sulfoalkyl chain, a saturated or unsaturated, branched or straight-chain $C_1$-$C_{50}$-alkyl chain, which optionally is interrupted by 0 to 15 oxygen atoms and/or by 0 to 3 carbonyl groups and/or is substituted with 0 to 5 hydroxyl groups;
- $R^5$ stands for a hydrogen atom, or a fluorine, chlorine, bromine or iodine atom, methyl, ethyl, propyl or isopropyl;
- b means the number 2 or 3; and
- X and Y, independently of one another, stand for O, S, $=C(CH_3)_2$ or —(CH=CH)—, or wherein the indocarbocyanine dye is Cy7, indocyanine green (ICG), an analog of ICG, or indotricarbocyanine (ITC)

as well as a salt or solvate thereof,
wherein no targeting moiety is attached to the dye.

6. A method according to claim 5, wherein the inflammatory joint disease is arthritis.

7. A method according to claim 6, wherein the arthritis is rheumatoid arthritis, osteoarthritis, psoriatic arthritis, traumatic arthritis, bacterial arthritis, post-infectious arthritis, lyme disease (Borreliose), ankylosing spondyliitis or rubella arthritis.

8. A method according to claim 5, wherein the indocarbocyanine dye is administered in an amount of 10 mg/kg body weight or less.

9. A method according to claim 5, wherein the indocarbocyanine dye is injected into the joint region to be diagnosed or into a blood vessel or the lymphatic system, which provides blood or lymph to the joint region of the body to be diagnosed.

10. A method according to claim 9, wherein the blood vessel is the vein of the arm.

11. A method according to claim 5, wherein the light in step (b) is applied continuously, amplitude modulated or pulsed.

12. A method according to claim 5, wherein the fluorescence is measured at multiple time points at least for 20 s, 30 s, 40 s, 50 s, 60 s, or 120 s after administration of the indocarbocyanine.

13. A method according to claim 5, wherein the fluorescence in the joint region is detected at each time point as one image and/or by scanning the joint region of the body.

14. A method according to claim 5, wherein the fluorescence is detected in intervals of 5 s or less.

15. A method according to claim 5, wherein a fluorescent standard is provided on or in the vicinity of the imaged joint region to normalize the measured fluorescence.

16. A method according to claim 5, wherein a computer program is used to determine a time resolved pattern of circulation, preferably a pattern of blood circulation within the joint region of the body.

17. A method according to claim 16, wherein the pattern of blood circulation in a patient suspected of having a joint inflammatory disease is compared to the pattern of blood circulation in a healthy patient and wherein alterations of the pattern of blood circulation are indicative of a joint inflammatory disease.

18. A method according to claim 5, wherein the joint region of the body is the hand, foot, knee, elbow or shoulder.

19. A method according to claim 18, wherein an increase of fluorescence at the joints is indicative of an inflammatory disease.

20. A method according to claim 5, wherein the indocarbocyanine wavelength of excitation maximum differs from the wavelength of the fluorescence maximum by at least 10 nm.

21. A method according to claim 4, wherein the indocarbocyanine dye is administered in an amount of 1 mg/kg body weight or less.

22. A method according to claim 4, wherein the indocarbocyanine dye is administered in an amount of 0.1 mg/kg body weight or less.

23. A method according to claim 1, wherein an increase of fluorescence is detected within less than 300 seconds after administration of the indocarbocyanine dye.

24. A method according to claim 5, wherein an increase of fluorescence is detected within less than 300 seconds after administration of the indocarbocyanine dye.

* * * * *

UNITED STATES PATENT AND TRADEMARK OFFICE
CERTIFICATE OF CORRECTION

| | | |
|---|---|---|
| PATENT NO. | : 7,879,314 B2 | Page 1 of 1 |
| APPLICATION NO. | : 11/476218 | |
| DATED | : February 1, 2011 | |
| INVENTOR(S) | : Licha et al. | |

It is certified that error appears in the above-identified patent and that said Letters Patent is hereby corrected as shown below:

Column 17, line 35, reads "SNH-, $SO_2$-, $PO_4^{31}$-, -aryl- and/or -NH-" should read -- SNH-, $SO_2$-, $PO_4^-$ -aryl- and/or -NH- --

Signed and Sealed this
Fifth Day of April, 2011

David J. Kappos
*Director of the United States Patent and Trademark Office*